United States Patent [19]

Smith

[11] Patent Number: 4,474,769

[45] Date of Patent: Oct. 2, 1984

[54] CHITOSAN AS A CONTRACEPTIVE

[75] Inventor: Robert L. Smith, Albany, Oreg.

[73] Assignee: Pfanstiehl Laboratories, Inc., Waukegan, Ill.

[21] Appl. No.: 494,509

[22] Filed: May 13, 1983

[51] Int. Cl.$^3$ .............................................. A61K 31/73
[52] U.S. Cl. ..................................... 424/180; 536/20
[58] Field of Search .......................... 424/180; 536/20

[56] References Cited

U.S. PATENT DOCUMENTS

| | | | |
|---|---|---|---|
| 2,831,851 | 4/1958 | Vogler | 536/20 |
| 3,862,122 | 1/1975 | Peniston et al. | 536/20 |
| 4,363,801 | 12/1982 | Nagyvary | 536/20 |
| 4,387,094 | 6/1983 | Bagros | 424/180 |

*Primary Examiner*—Johnnie R. Brown
*Attorney, Agent, or Firm*—Sidney Wallenstein; Harry V. Strampel

[57] ABSTRACT

A method of contraception comprising placing in the uterine cavity a contraceptively effective amount of chitosan, advantageously in a carrier, and retaining the chitosan in the uterine cavity for a prolonged period of time to kill or inactivate mammalian spermatazoa.

21 Claims, No Drawings

CHITOSAN AS A CONTRACEPTIVE

The present invention relates to the field of contraception and is specifically concerned with preventing fertility in mammals, particularly the human female, by means of the use of locally applied chitosan, to-wit, in the uterine cavity, in a form effective to prevent the fertilization of the ovum by the spermatozoa, particularly human male sperm under conditions and in a form such as to prevent conception.

It has long been known to prevent fertility in human and other animal females by locally acting agents since their use, if at least reasonably effective, avoids the problems and complications which not infrequently result from such procedures as utilize mechanical devices such as intrauterine shields which are placed into the uterus, or systemically acting compositions such as the orally administered steroid hormones or birth control pills. Such mechanical devices have numbers of disadvantages and the same is true of the use of steroids, which disadvantages are well known to the art.

Many locally applied contraceptive agents have long been known or suggested by the art, including various metal compounds, and spermacide-containing compositions which are inserted in the vagina shortly prior to intercourse and which generate a spermacide-containing foam. The deficiencies of such metal compounds and spermacide-containing compositions are, likewise, well known to the art.

In accordance with the present invention, chitosan is utilized as a spermatastat which prevents the spermatazoa from penetrating and fertilizing the ovum and is applied locally by insertion in the uterine cavity in the manner described below.

Chitosan is deacetylated chitin. Chitin, the source material for citosan, is a cellulose-like polymer present in fungal cell walls and exoskeletons of arthropods such as insects, crabs, shrimps and lobsters, and it is produced in large quantities particularly from waste shells of crabs and shrimps. Depending upon its molecular weight, it is soluble or insoluble in water. Likewise, based upon its molecular weight, its solubility varies in different commercial solvents.

Chitosan, which, as stated above, is prepared by deacetylating chitin, is soluble in dilute formic, acetic, pyruvic, lactic and malic acids, and inorganic acids, were the solute is water, water-methanol, water-ethanol, water-acetone and similar diluents. In various acidic solvents, chitosan forms viscous non-Newtonian solutions. The solution viscosities of chitosan depend upon its molecular weight, the extent of deacetylation of the chitin, concentration and types of solvents, and temperature. As solution temperature increases, viscosity decreases. Viscosity retention is compatible with that of carboxymethyl cellulose. The foregoing facts are well known to the art.

Chitosan has heretofore been used and/or suggested for use for a wide variety of purposes, including, by way of illustration, for flocculating bacteria, yeasts and microfungi from suspensions containing the same; for flocculation of industrial wastes such as proteins in liquid wastes from packing houses, poultry, fish and vegetable processing plants, whey, leather tanning wastes, Kraft paper mill wastes and suspended solids from mine tailings; for preparing membranes which have ion exchange properties and with various permeability properties in regard to moisture and gases such as oxygen, nitrogen and carbon dioxide; for chelation and for column chromatography metal, enzyme and virus separation procedures; as viscosity builders for various foods, cosmetics, drugs, etc.; for broad spectrum antifungal uses such as preventing the growth of pathogenic fungi which normally infect peas and other plant products; for inhibiting the fermentation of yeasts in various food products; and for application to seeds prior to planting to prevent fungal diseases. It is also known that chitosan solutions are similar in certain of their characteristics and properties to cellulose ethers, functioning as thickeners, stabilizers and suspending agents. Based upon tests reported in the literature, chitosan is non-toxic and, indeed, is found in and has been used and suggested, as noted above, for use in various food products.

While chitosan is found in the cell walls of some fungi, it is prepared commercially by deacetylation of chitin in a variety of known ways such as, for instance, by certain plant enzymes. The extent of deacetylation of chitin to produce chitosan is variable. For use of chitosan for the contraceptive purposes of the present invention, it is unnecessary that the chitin be deacetylated sufficiently to allow dissolving it in the recommended solvent. A commercially available partially deacetylated chitin is partially deacetylated (about 16%) glucoseamine polymer, $\beta$-(1-4)2-acetamido-2-deoxy-$\delta$ glucose, which is acetylated chitin containing about 7.5% nitrogen, and being about 80% deacetylated. Chitosans having higher percentages of deacetylation can be used, as well as lower percentages of deacetylation, but, generally speaking, it is preferred that the percentage of deacetylation do not fall lower than about 65%. The unreacted chitin is not harmful but it is fundamentally inert in its contraceptive properties and, therefore, relatively high percentages of chitin in the chitosan are undesired.

In order for the chitosan to act most effectively to prevent the sperm from penetrating the ovum, the chitosan molecules must be motile. For this reason, for optimum results, the chitosan molecules should be in the form of a solution or the like as distinguished from being used in powder form. As indicated above, where the chitosan is in a form in which it is insoluble in water, it is conveniently used by dissolving it in dilute solutions of non-toxic acidic materials and acids which are also non-irritating to the delicate tissue of the walls of the intrauterine cavity. Dilute solvent solutions of chitosan in such acids as, for example, formic, acetic, propionic, butyric, malic, fumaric, succinic, pyruvic, lactic, acetic, D-Glucuronic, D-Galacturonic and D-Mannuronic acids afford functionally effective compositions for use in accordance with the present acid. While dilute inorganic acid solutions of chitosan can also be used, from a functional standpoint, their use is distinctly less preferable because of the generally adverse effect of the inorganic acids on the tender tissues of the walls of the intrauterine cavity. Especially satisfactory as a solvent for the chitosan is ascorbic acid since it tends to provide for better penetration of the chitosan and to be tolerated more satisfactorily by the body than at least most of the other acids.

The amount of the acidic material or acid required to dissolve the chitosan is variable, depending upon the particular chitosan utilized, within wide limits, as, for instance, from 5 ppm to 10%. Once the chitosan is dissolved, it can be diluted to a very low level, depending on the manner in which the chitosan composition is utilized. If it is to be employed in the form of a gel, the chitosan content of the contraceptive composition can be in the range of about 1% to about 5%, by weight, in aqueous solutions of, for instance, 1% to 3% of acetic acid or ascorbic acid. If the chitosan serves to provide all of the gelling action, the higher levels of chitosan disclosed above are particularly desirable. If a separate gelling agent is used, then levels of chitosan lower than 1% can be employed. Over and above such use where it is placed into the intrauterine cavity for retention over relatively prolonged periods of time, the chitosan compositions can also be used as douches in which case, by way of illustration, suitable formulations can comprise from about 0.25% to about 1.5%, by weight, in aqueous solutions of, for instance, 0.25% to 1.5% of acetic acid or ascorbic acid.

The concentration of the chitosan in the solution or the gel for preventing conception is variable and, in general, will range from a level of about 5% down to about 10 ppm. In this connection, it is important to taken into account that the chitosan tends to be tied up by the proteins which are present in the vagina and uterus as a result of the seepage of such proteins into the solutions or gels in the intrauterine cavity. There is, therefore, required to be sufficient chitosan available in the vagina and uterus to overwhelm the mucal proteins which are present and still leave sufficient chitosan molecules to inactivate or tie up the enzymes present which would otherwise allow the sperm to penetrate the ovum.

Another factor which is to be taken into account is the molecular weights of the chitosans which are utilized. The molecular weights, generally speaking, of the chitosans as produced or which are normally produced will tend to fall within the range of about 30,000 to about 300,000. High molecular weight chitosans form solutions with higher viscosities than chitosans of lower molecular weight. With high molecular weight chitosans, say about 300,000, a gel is produced in dilute aqueous solutions of acidic materials or acids with as little as 1%, by weight, of such chitosans. On the other hand, with chitosans having molecular weights as low as about 30,000, in dilute aqueous acidic or acid solutions, about 5% to about 10% solutions, by weight, of such chitosans produce solutions having a relatively low viscosity.

It will, of course, be recognized that the chitosan, in the form of solutions or gels, can be incorporated with other materials to produce compositions having variant viscosities, as well as with supplemental materials such as perfumes and colorants, as well as active ingredients.

I claim:

1. A method of contraception which comprises placing a contraceptively effective amount of chitosan into the uterine cavity of a female animal prior to implantation of a fertilized ovum.

2. The method of claim 1 in which the female animal is a human and the ovum is a human ovum.

3. A method according to claim 2 wherein said chitosan is present in a carrier effective to retain it in the uterine cavity over a period of time sufficient to prevent the fertilization of the ovum by spermatozoa.

4. A method according to claim 2 wherein the chitosan is present in the uterine cavity in the form of a carrier comprising a non-toxic acidic medium.

5. A method according to claim 4 in which the carrier comprises an acid.

6. The method of claim 5 in which the carrier is ascorbic acid.

7. The method of claim 6 in which the chitosan is in the form of a solution in ascorbic acid.

8. The method of claim 5 in which the chitosan is in the form of a solution in acetic acid.

9. A method of contraception in which chitosan in a motile form is placed in a contraceptually effective amount into the uterine cavity of a female animal prior to implantation of a fertilized ovum.

10. The method of claim 9 in which the female animal is a human and the ovum is a human ovum.

11. The method of claim 10 in which the concentration of the chitosan is present in a solution in a non-toxic acidic medium and in a concentration in the range of 10 ppm to 5%.

12. The method of claim 10 in which the chitosan is inserted in the uterine cavity in the form of an aqueous-containing acidic solution in a concentration in said solution of about 0.25% to about 1.5%.

13. The method of claim 10 in which the chitosan is inserted in the uterine cavity in the form of an aqueous-containing gel in a concentration in said gel of about 1.5 to about 10%.

14. The method of claim 10 in which the molecular weight of the chitosan lies within the range of about 30,000 to about 300,000.

15. A method for killing mammalian spermatozoa which comprises contacting said spermatozoa with a spermicidally effective amount of chitosan by placing said chitosan within the uterine cavity of a female animal prior to the implantation of a fertilized ovum.

16. The method of claim 15 in which the chitosan is applied on or in a non-toxic acidic carrier.

17. The method of claim 16 in which the spermatazoa are human spermatazoa.

18. The method of claim 17 in which the acidic carrier is an organic or inorganic acid.

19. The method of claim 18 in which the acid is ascorbic acid.

20. The method of claim 18 in which the acid is acetic acid.

21. A method of inactivating mammalian spermatozoa which comprises contacting said spermatozoa with a spermatastatically effective amount of chitosan by placing said chitosan within the uterine cavity of a female animal prior to the implantation of a fertilized ovum.

* * * * *